United States Patent
Alfano et al.

(10) Patent No.: US 7,145,148 B2
(45) Date of Patent: Dec. 5, 2006

(54) SYSTEMS AND METHODS FOR NON-DESTRUCTIVELY DETECTING MATERIAL ABNORMALITIES BENEATH A COATED SURFACE

(76) Inventors: Robert R. Alfano, 3777 Independence Ave., Bronx, NY (US) 10463; Baolong Yu, 389E. 194th St., Apt. 2, Bronx, NY (US) 10458

( * ) Notice: Subject to any disclaimer, the term of this patent is extended or adjusted under 35 U.S.C. 154(b) by 0 days.

(21) Appl. No.: 10/949,571

(22) Filed: Sep. 24, 2004

(65) Prior Publication Data

US 2005/0098728 A1    May 12, 2005

Related U.S. Application Data

(60) Provisional application No. 60/505,441, filed on Sep. 25, 2003.

(51) Int. Cl.
*G01J 5/02* (2006.01)
*G01N 21/88* (2006.01)
*G01N 21/47* (2006.01)

(52) U.S. Cl. ............... 250/341.8; 250/339.11; 250/358.1

(58) Field of Classification Search ............. 250/341.8, 250/330, 339.11; 702/40
See application file for complete search history.

(56) References Cited

U.S. PATENT DOCUMENTS

| | | | |
|---|---|---|---|
| 5,703,362 A * | 12/1997 | Devitt et al. ............. | 250/341.8 |
| 6,184,528 B1 * | 2/2001 | DiMarzio et al. ...... | 250/339.08 |
| 6,495,833 B1 * | 12/2002 | Alfano et al. .......... | 250/341.08 |
| 6,853,926 B1 * | 2/2005 | Alfano et al. ................. | 702/40 |
| 2004/0026622 A1 * | 2/2004 | DiMarzio et al. ........ | 250/341.8 |
| 2004/0065832 A1 * | 4/2004 | Cluff et al. .............. | 250/341.1 |
| 2004/0095147 A1 * | 5/2004 | Cole .......................... | 324/629 |
| 2004/0119018 A1 * | 6/2004 | Alfano et al. ............ | 250/341.1 |

* cited by examiner

*Primary Examiner*—David Porta
*Assistant Examiner*—Frederick R. Rosenberger
(74) *Attorney, Agent, or Firm*—Dilworth & Barrese LLP

(57) ABSTRACT

The present invention provides systems and methods for non-destructively detecting material abnormalities beneath a coated surface. A terahertz (THz) illumination unit illuminates an area of the coated surface. A detection unit detects light reflected from the illuminated area of the coated surface, and a processing unit images the illuminated area of the coated surface from optical characteristics received from the detection unit.

9 Claims, 7 Drawing Sheets

SYSTEMS AND METHODS FOR NON-DESTRUCTIVELY DETECTING MATERIAL ABNORMALITIES BENEATH A COATED SURFACE

This application claims priority under 35 U.S.C. § 119 to a provisional application entitled "Terahertz Transmission Window to Detect and Image Corrosion, Defects and/or Cracks Beneath Paint or Primer, Coatings Layers of a Surface" filed in the United States Patent and Trademark Office on Sep. 25, 2003 and assigned Ser. No. 60/505,441, the contents of which are hereby incorporated by reference.

GOVERNMENTAL INFORMATION

This invention is supported in part by: New York State Office of Science, Technology and Academic Research.

BACKGROUND OF THE INVENTION

1. Field of the Invention

The present invention relates generally to systems and methods for non-destructively detecting material abnormalities beneath a surface, and in particular, to systems and methods for detecting corrosion and cracks in metal surfaces beneath a layer of paint using a terahertz (THz) imaging technique.

2. Description of the Related Art

Paint or other coatings are typically applied to surfaces to protect the surfaces against corrosion or other damage. In some instances, corrosion, cracking, or other damage (material abnormality) begins under the paint or coating and is undetectable by visual inspection. In addition, the paint itself may crack, while the underlying surface is perfectly fine. This may cause unnecessary repairs. Conventionally, inspections may be carried out by one or more of the following non-destructive imaging (NDI) techniques.

Ultrasonic (pulse echo or through transmission) methods can monitor larger defects of, for example, aircraft structures for a whole field, but are not preferred for detection of early or surface deterioration. The techniques are particularly conducive to rapid imaging of a surface and include magneto-optic eddy current imaging, active thermography, optically aided visual inspection, and spectral imaging.

Magneto-optic imaging (MOI) can image corrosion and cracks over a small area the size of the magneto-optic crystal plate used in a hand-held scanner. However, MOI's sensitivity to top-surface corrosion depends on the degree to which the eddy currents are altered and gives rise to anomalies in the induced magnetic field at the surface. It has not been shown conclusively that the MOI technique can detect incipient corrosion that has not yet produced a significant increase in macroscopic surface roughness.

Active Thermography (AT) is an increasingly important technique for detecting subsurface flaws such as delamination, debonding, and second-surface corrosion. AT has a lower sensitivity to incipient corrosion under paint, however, because (1) the initial stages of corrosion do not significantly increase the thermal impedance of the surface compared to a layer of paint alone, and (2) the detailed resolution of incipient corrosion effects at the top surface requires a very high speed infrared camera to resolve surface transients which may appear only in the few milliseconds after the initial flash lamp illumination. In addition, such equipment is prohibitively expensive for use on a wide scale. However, for significant surface corrosion, AT and MOI have the potential to image significant surface corrosion damage and distinguish it from subsurface effects by employing commercially available instrumentation.

Visual Inspection (VI) is used to determine the extent of corrosion damage on a skin of a surface and around fasteners, for example, after the paint or coating has been stripped. As a nondestructive technique for painted aircraft, visual techniques are not amenable to detection of chemical changes or micro-roughness at the paint/metal interface, unless significant corrosion products penetrate through the thickness of the paint.

Spectral Imaging (SI) techniques using near-infrared (NIR) and mid-infrared (MIR) light generally use a compact multi-spectral imaging sensor. This method is based on the partial transparency of many aircraft paints to specific bands of infrared radiation. Using this method, it is possible to detect changes in the chemistry of the metal surface or the primer by analyzing the amplitude of reflected and emitted radiation at specific wavelengths. The layered depth information, i.e., the state of the surface at different depths below the paint, cannot be deduced from a simple SI approach, however.

Photonic techniques offer a potentially rapid, noninvasive and easy approach to detect corrosion and cracks in situ. Art preservationists use Near-IR (NIR) charge-coupled device (CCD) cameras ($\lambda < 2$ µm) to view paintings that have underdrawings not visible with the human eye. Novel methods of a second-harmonic generation (SHG) imaging, and spectral polarization optical imaging have been proposed to detect the early stages of corrosion under thin layers of paint using NIR. One such example of this technique can be found in U.S. Pat. No. 6,495,833, entitled "Sub-surface Imaging Under Paints and Coatings Using Early Light Spectroscopy," which issued to Alfano et al. on Dec. 17, 2002 (hereinafter referred to as "Alfano").

Alfano discloses near-infrared (NIR) optical imaging systems and methods to non-destructively image (NDI) deteriorations or defects in painted metals and artwork beneath painted surfaces. Specfically, back-scattered light is used to determine suitability to monitor corrosion and cracking in metal beneath paints, up to a thickness of about 500 µm. That is, NIR light, which is in the paint transmission zone spanning from 800 nm to 2,000 nm, can be used to assess the quality of metallic structures below the paint level for incipient and advanced stages of corrosion and cracking. NIR light scattered from paint, corrosion, air voids, and metal can be spatially imaged in micrometer sliced subsurface layers. In addition, spectral, temporal, spatial, non-linear optical, and polarization gates are employed to distinguish phantoms in turbid media, such as painted corroded metal and cracked specimens, e.g., painted surfaces from airplanes, submarines, ships, automobiles, bridges, etc.

However, the systems and methods disclosed in Alfano, which utilize NIR/MIR optical imaging, also require a gating system in order to create the detected images. This gating system tends to create a more complex and costly imaging system. In addition, this method is not capable of detecting the early stages of corrosion under surface thick paint with thickness larger than 40 µm.

In U.S. patent application Ser. No. 10/455,662, entitled "Systems and Methods for Non-Destructively Detecting Material Abnormalities Beneath a Coated Surface", which was also filed by Alfano et al., (hereinafter referred to as "Alfano II"), systems and methods are disclosed for detecting the early stages of corrosion under surface thick paint with thickness larger than 40 µm. In Alfano II, a mid-infrared (MIR) 2 µm to 8 µm detection unit illuminates an area of a coated surface and detects light reflected from the illuminated area of the coated surface, and a processing unit for produces an image from optical characteristics received from the MIR detection unit. However, in Alfano II, the processing of the optical characteristics requires extra time and resources, which adds to the complexity and cost associated with those systems and methods.

Therefore, in U.S. patent application Ser. No. 10/653,473, entitled "Systems and Methods for Non-Destructively Detecting Material Abnormalities Beneath a Coated Surface", which was also filed by Alfano et al., (hereinafter referred to as "Alfano III"), improved systems and methods are disclosed for detecting the early stages of corrosion under surface thick paint with thickness larger than 40 μm. In Alfano III, a mid-infrared (MIR) illumination unit for illuminates an area of the coated surface, and an MIR optical 2-D imager for images the illuminated area of the coated surface.

However, zinc rich primer and metallic based paints and coatings are commonly used on bridges, airplanes, boats and ships. Further, due to strong absorption and small depth of penetration in these kinds of paints or primers, for visible, NIR, and MIR radiations, it is impossible to obtain a clear image for these samples with metallic paint, especially coated by zinc rich primer. Accordingly, a need exists for an improved system and method for inspecting surfaces through a coating, such as zinc rich primer and metallic based paints. A further need exists for such a system and method, which improves upon existing techniques.

SUMMARY OF THE INVENTION

It is, therefore, an object of the present invention to provide a system and method for detecting corrosion and cracks in metal surfaces beneath a layer of paint using a terahertz (THz) imaging technique.

To achieve the above and other objects, the present invention provides a system for non-destructively detecting material abnormalities beneath a coated surface. Preferably, the system includes: a terahertz (THz) illumination unit for illuminating an area of the coated surface; a detection unit for detecting light reflected from the illuminated area of the coated surface; and a processing unit for imaging the illuminated area of the coated surface.

In addition, the system may further comprise a scanning unit for moving the THz illumination unit and/or an optical 2-D imager to a next area.

To achieve the above and other objects, the present invention also provides a method for non-destructively detecting material abnormalities beneath a coated surface. Preferably, the method includes the steps of: illuminating an area of the coated surface by a terahertz (THz) light source; detecting light reflected from the illuminated area of the coated surface; and imaging the surface below the illuminated area of the coated surface.

Additionally, the method may further comprise scanning a next area.

BRIEF DESCRIPTION OF THE DRAWINGS

The above and other objects, features, and advantages of the present invention will become more apparent from the following detailed description when taken in conjunction with the accompanying drawings in which.

DETAILED DESCRIPTION OF PREFERRED EMBODIMENTS

Figure 1:
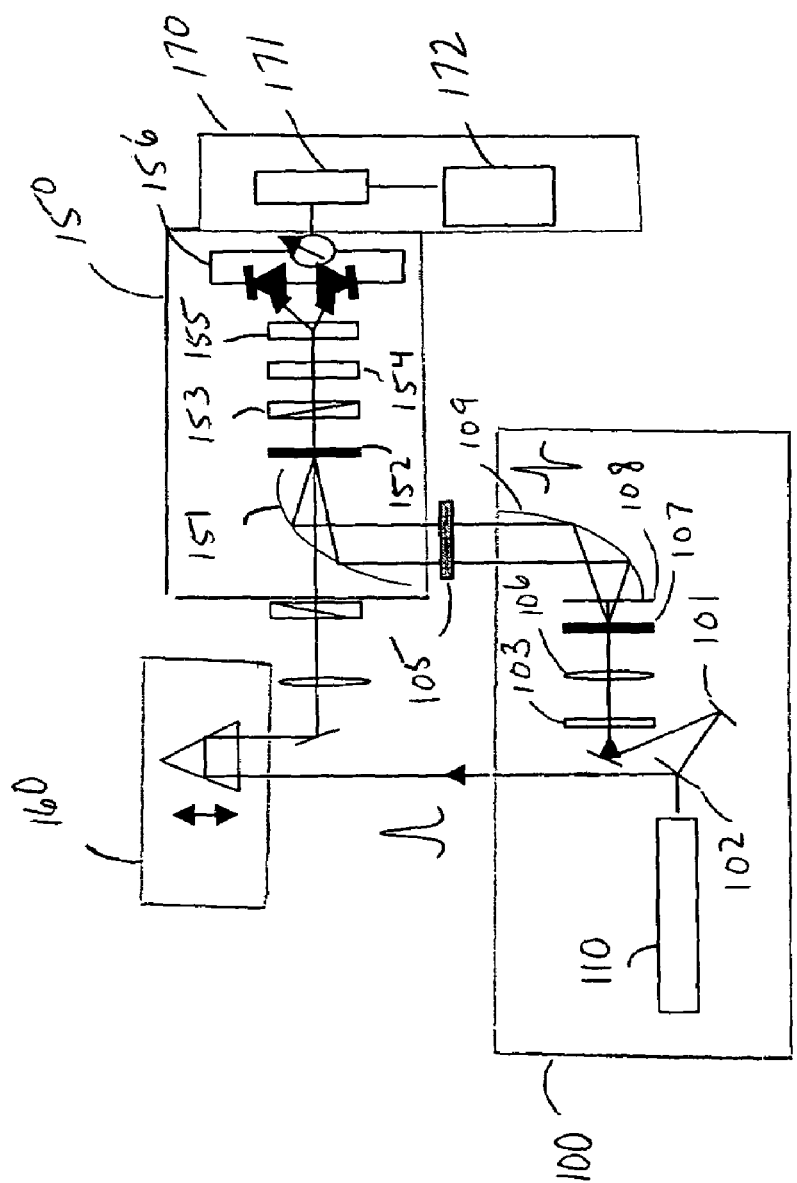
FIG. 1 is a diagram illustrating a system for measuring an optical transmission of a paint according to an embodiment of the present invention.

Several preferred embodiments of the present invention will now be described in detail herein below with reference to the annexed drawings. In the drawings, the same or similar elements are denoted by the same reference numerals even though they are depicted in different drawings. In the following description, a detailed description of known functions and configurations incorporated herein has been omitted for conciseness.

As indicated above, metallic based paints and coatings are commonly used on bridges, airplanes, boats and ships. Therefore, it has become increasingly important to study the absorption and dispersion of metallic based paint and zinc rich primer using a THz source. A THz beam is a new source with a wide frequency range of 0.1–30 THz (10μm–3 mm), which can be generated using 30–200 fs optical pulses via optical rectification or using other methods such as fast switches and quantum well semiconductor devices.

Recent experimentation has shown that the THz time-domain spectroscopy (THz-TDS) is an ideal tool for spectroscopic measurements of far-infrared to microwave properties of materials such as dielectrics, semiconductors, superconductors, biological materials, liquids, and gases. Most chemical compounds show very strong, highly specific frequency-dependent absorption and dispersion in the THz range. The propagation of THz pulses leads to characteristic time-domain waveforms when THz radiation passes through different materials. Additionally, it is feasible to apply THz-TDS to determine the chemical content of an unknown object.

Together, with the ability to collimate and focus THz beams down to the diffraction limit of a few hundred micrometers at the sample, imaging of chemical compositions should be possible with reasonable spatial resolution by the THz-TDS technique.

Accordingly, in accordance with the present invention, the THz transmittance curves for different types of paints, coatings, and primers are presented. Different transmissions were found for different paints and primers in the THz region. Due to small absorption of metallic or non-metallic based paints and primers in THz range, THz beam can penetrate these metallic based paints and primers to form and obtain an image to detect material abnormalities below the painted surface, such as corrosion, defects, and/or cracks on a subsurface. By the focusing THz beams down to the diffraction limit of 10–30 micrometers at a sample, the ability of imaging of corrosion and/or cracks on a metallic surface beneath a primer or metallic based paint was found using a THz reflection imaging technique. More specifically, the present invention teaches how to use THz beam to image defects, corrosion and/or cracks under dielectrics, polymers, metallic paints, and coatings.

As described above, THz beams can penetrate various types of paints, coatings, and primers. That is, the THz pulse can be used to form an image of the corrosion and/or cracks on a metallic surface beneath a paint or primer using THz radiation and reflection imaging technique. To test the concept, the absorption spectrum of strontium chromate epoxy primer (Mil-P-23377) and an inorganic zinc rich primer (Dimetcote D9 HS) have been measured in the frequency range 0.2 to 2.0 THz (10–66 cm$^{-1}$).

FIG. 1 is a diagram illustrating a system for measuring an optical transmission of a paint according to an embodiment of the present invention. Referring to FIG. 1, the system includes a THz illumination unit 100, a detection unit 150, a time delay 160, and a processing unit 170. The THz illumination unit 100 creates and directs THz light (radiation) to a sample 105, which is a substrate that is at least partially coated with the paint being tested. The THz light passes through the sample 105 and is detected by the detection unit 150. Additionally, the THz illumination 100 transmits the THz light to the time delay 160, which then transmits the delayed THz light to the detection unit 150. The detection unit 150 detects received THz light and transmits detected signal information to the processing unit 170, which processes the signal information in order to determine the optical transmission of the paint.

The THz illumination unit 100 includes a fast laser light source 110 such as fs, ps or ns lasers (solid state, semiconductor, Cr$^{4+}$:YAG, fiber) and beam focusing elements. For example, in FIG. 1, the beam focusing elements include mirrors 101 and 102, a chopper 103, a lens 106, an optical rectifier 107, a silicon filter 108, and a parabolic mirror 109. The beam focusing elements focus (or direct) the THz light to the sample.

The time delay unit 160 includes mirrors and controlled translation stages and is used to delay the laser pulse.

The detection unit 150, like THz illumination unit 100, also includes beam focusing elements and includes a balanced detector 156. The beam focusing elements focus/direct the THz light that has passed through the sample 105 to the balanced detector 156. For example the beam focusing elements may include a parabolic mirror 151, a nonlinear semiconductor crystal 152, such as ZnTe, GaSe, GaAs or other alloy semiconductors, a polarizer 153, a quarter wave plate 154, and a Wollaston prism 155. The balanced photo detector 156, which preferably consists of two photodiodes, detects the received signals and produces detected signal information, which is transmitted to the processing unit 170.

The processing unit 170 may include a lock-in amplifier 171 for processing the detected signal information received from the detection unit, and a computer 172 for digitizing and storing the processed signals for further computation and/or analysis. From the processed signals, it is possible to determine the transmittance of the paint at different frequencies.

Hereinbelow, a description will be given of an operation for determining the transmittance of a paint sample using the system illustrated in FIG. 1.

Preferably, the THz light source 110 is a mode-locked Ti:sapphire amplifier system that provides 200-fs pulses at a wavelength of 800 nm with a repetition rate of 250 kHz. Additionally, it is preferable that the THz light is produced by optical rectification in a nonlinear medium. The optical rectification is performed by the optical rectifier 107, which can be embodied as a ZnTe crystal via second order non-linearity coefficient $\chi^{(2)}$.

The electric field of the THz pulses after passing through the sample is detected in the crystal 153, which can be embodied as a second ZnTe crystal, via electro-optic sampling.

As illustrated in FIG. 1, the sample 105 is positioned between the THz illumination unit 100 and the detection unit 150. In actual lab experimentation, the system was enclosed in dry nitrogen purged boxes to diminish the THz absorption due to ambient humidity. Pulses of different optical duration from ps to fs in the far infrared region can be produced and detected using $\chi^{(2)}$ material.

Figure 2:
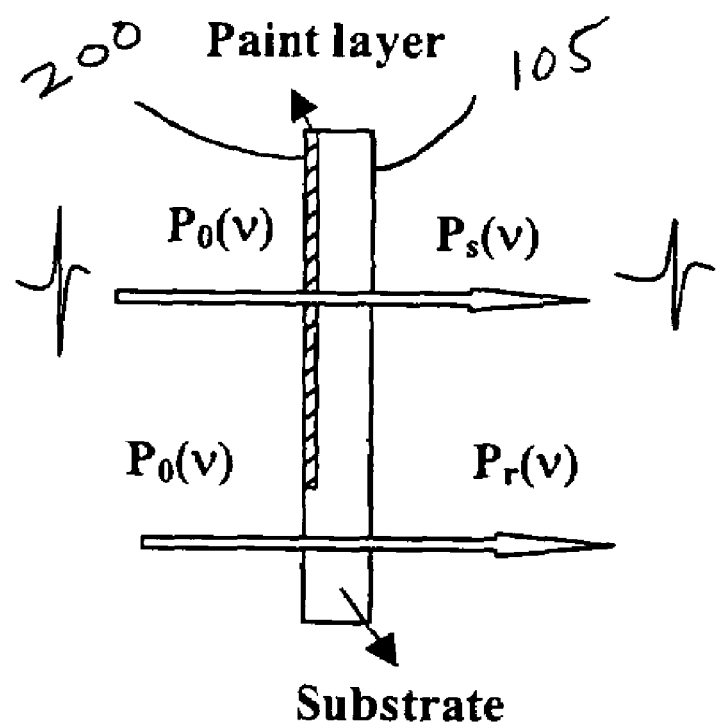
FIG. 2 is a cross-sectional view of a sample deposited on a polyethylene substrate to measure an optical transmission of a paint system according to the first embodiment of the present invention.

FIG. 2 is a cross-sectional view of a sample deposited on a polyethylene substrate to measure an optical transmission of a paint according to the first embodiment of the present invention. The sample 105 includes a paint layer 200 deposited on the polyethylene substrate to measure the optical transmission of the paint against frequency (wavelength). Assuming the non-absorbing substrate has a refractive index of $n_s$=1.52±0.01 at 300 K, the transmittance of the paint at different frequencies T(v) can be calculated from Equation (1).

$$T(v) = \frac{4n_p^2(1+n_s)^2}{(1+n_p)^2(n_p+n_s)^2} \cdot \frac{P_s(v)}{P_r(v)} \quad (1)$$

In Equation (1), $P_s(v)$ and $P_r(v)$ are the transmitted powers of the THz light through the paint layer 200 and a reference, i.e., the non-covered portion of the substrate, respectively. $n_p$ is the group refractive index of paint. Preferably, the thickness of the polyethylene substrate is approximately 4.0 mm to avoid interference peaks in the THz profile in the studied time zone arising from multiple reflections from the two surfaces of the polyethylene substrate.

After determining the transmittance of the paint, it is possible to use THz-TDS to image material abnormalities in structures under the paint.

Figure 3:
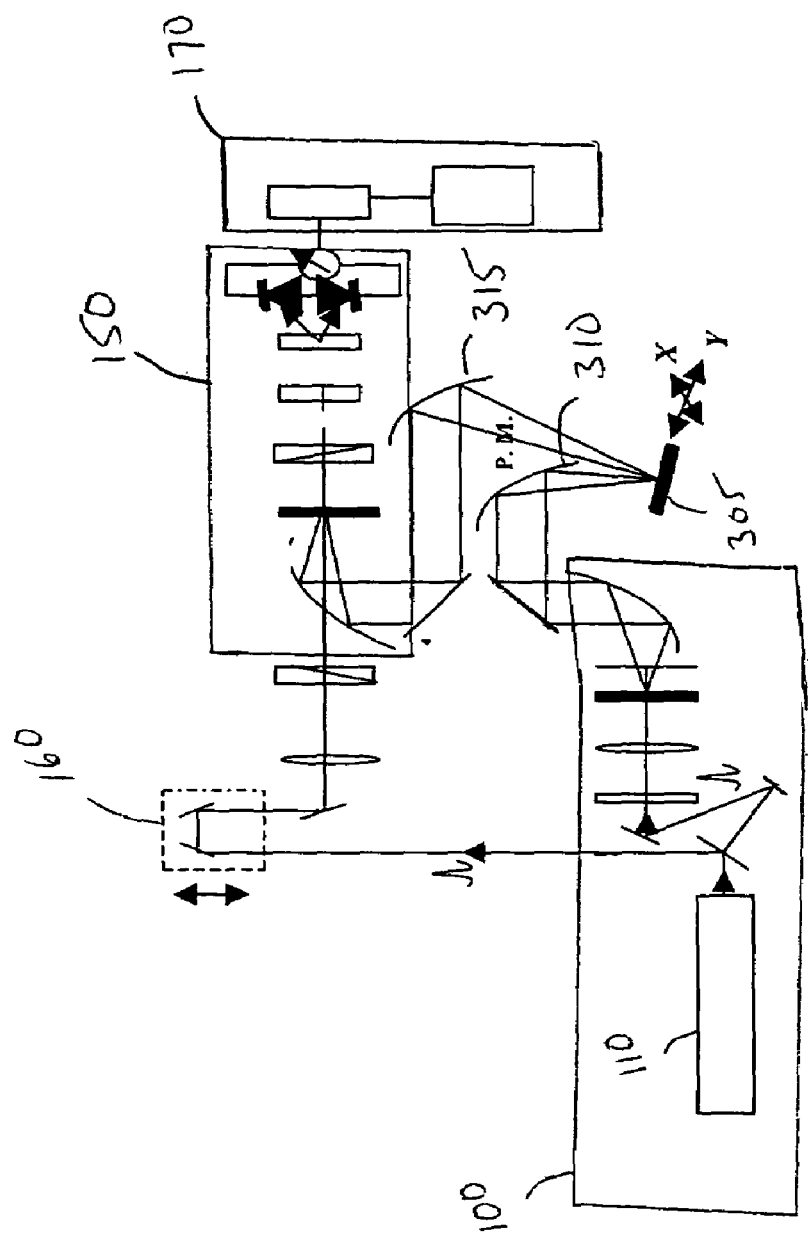
FIG. 3 is a diagram illustrating a detection system according to a second preferred embodiment of the present invention.

FIG. 3 is a diagram illustrating a detection system according to a second preferred embodiment of the present invention. More specifically, FIG. 3 illustrates a setup for detecting and imaging material abnormalities such as corrosion and/or cracks beneath the thick paint layer or zinc rich primer (up to 200 μm thick) using a THz scanning reflection imaging technique by scanning the beam on a moveable sample. As described above, the previously used NIR and MIR radiations do not pass through this type of paint.

Referring to FIG. 3, the detection system includes a THz illumination unit 100, a detection unit 150, a time delay 160, and a processing unit 170. Additionally, because these structures are substantially identical to those described in FIG. 1, a detailed description thereof will not be given again.

In FIG. 3, however, because the sample 305 is not placed between the THz illumination unit 100 and the detection unit 150, as in FIG. 1, the THz illumination unit 100 and the detection unit 150 illustrated in FIG. 3 also included parabolic mirrors 310 and 315, respectively. Parabolic mirror 310 is used to focus the THz light onto a specific point of the sample 305, and the parabolic mirror 315 is used capture and direct the reflected THz light from the sample into the detection unit 150. Accordingly, back reflection geometry is used to image the subsurface structure of the corroded samples coated with paint or primer by scanning the beams.

Additionally, in FIG. 3, the lock-in amplifier 171 processes signals received from the detection unit 150, and the computer 172 digitizes and stores the processed signals to produce a 2-D image of the scanned area. The 2-D image of the scanned area can then be stored in a memory of the computer and/or displayed on a display, such as monitor.

In order to increase the imaging area of the system illustrated in FIG. 3, the system may also includes an X-Y scanning system, which may comprise sliding stages, to move the THz illumination unit 100 and the detection unit 150 relative to the sample 305.

Figure 4:
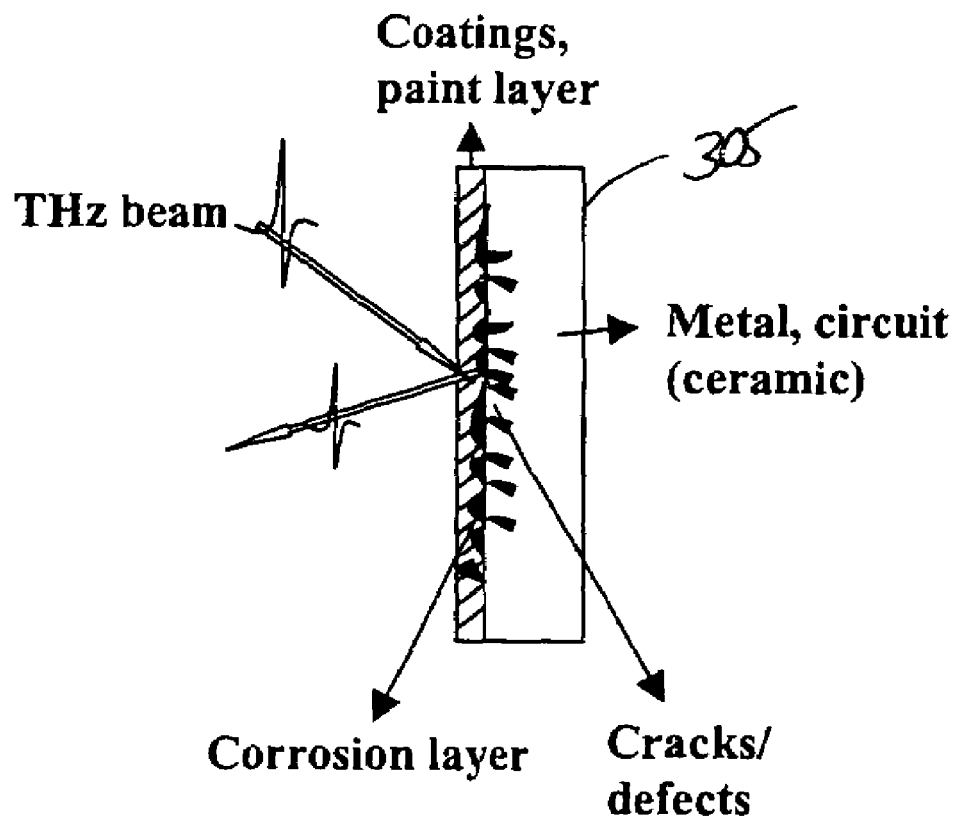
FIG. 4 is a cross-sectional view of a sample deposited on a polyethylene substrate to measure an optical transmission of a paint system according to the second embodiment of the present invention.

FIG. 4 is a cross-sectional view of a sample deposited on a polyethylene substrate to measure an optical transmission of a paint system according to the second embodiment of the present invention. Referring to FIG. 4, the THz light focused to a diffraction-limited spot on the sample 305, and the reflected THz waveforms are acquired and processed in real time at each point of the sample. Preferably, the sample is scanned in x and y directions at a rate of approximately 10–20 pixels/s to form an image in the computer 172. By analyzing the temporal waveform reflected from the sample 305 at every pixel of the object in real time, information on the surface of the sample 305 can be inferred in many cases. Information under coatings of circuit boards, computer chips, bridges, boats, etc., about defects can be obtained using THz-TDS.

In lab experimentation, the THz transmittance spectra of paints and primers were obtained by measuring the transmitted power of $P_s(v)$ and $P_r(v)$ by THz-TDS and calculating $T(v)$ using Equation (1) at room temperature.

Figure 5:
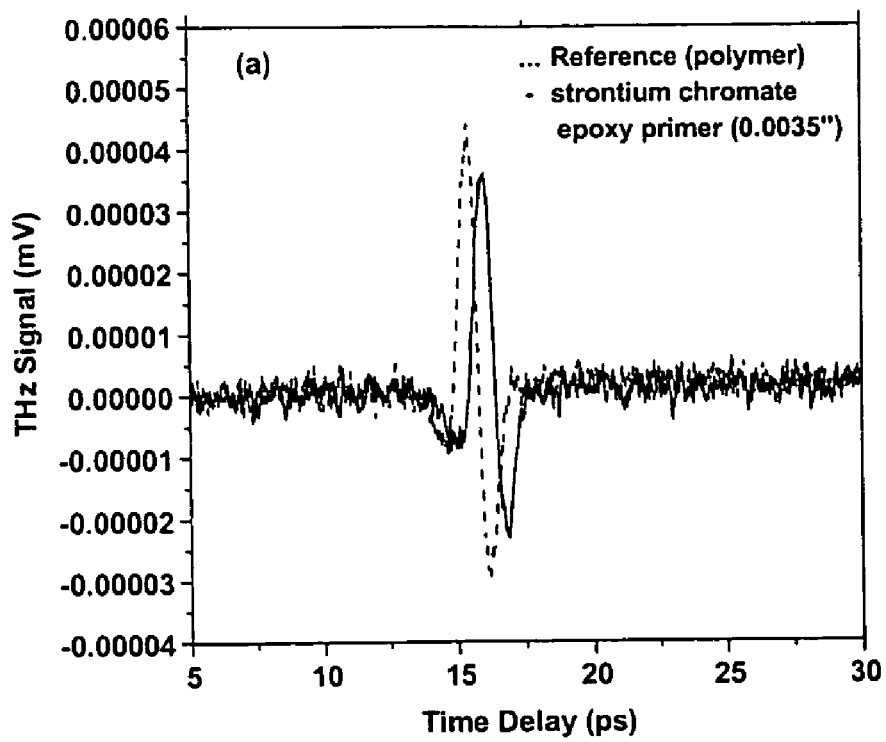
FIG. 5 is a graph illustrating THz temporal profiles of strontium chromate epoxy primer (Mil-P-23377) after passing through a pure polymer polyethylene substrate as reference.

FIG. 5 is a graph illustrating the THz temporal profiles of strontium chromate epoxy primer (Mil-P-23377) after passing through a pure polymer polyethylene substrate as reference.

Figure 6:
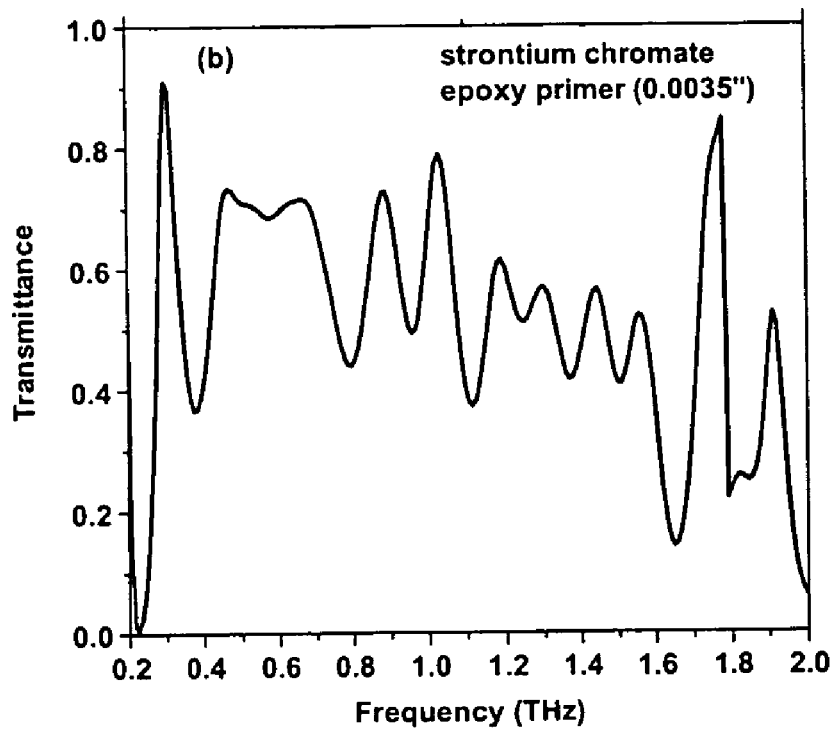
FIG. 6 is a graph illustrating THz transmitted profiles through a primer.

FIG. 6 is a graph illustrating the THz transmitted profiles through primer layer. The transmission through the paint is more than 40%.

Figure 7:
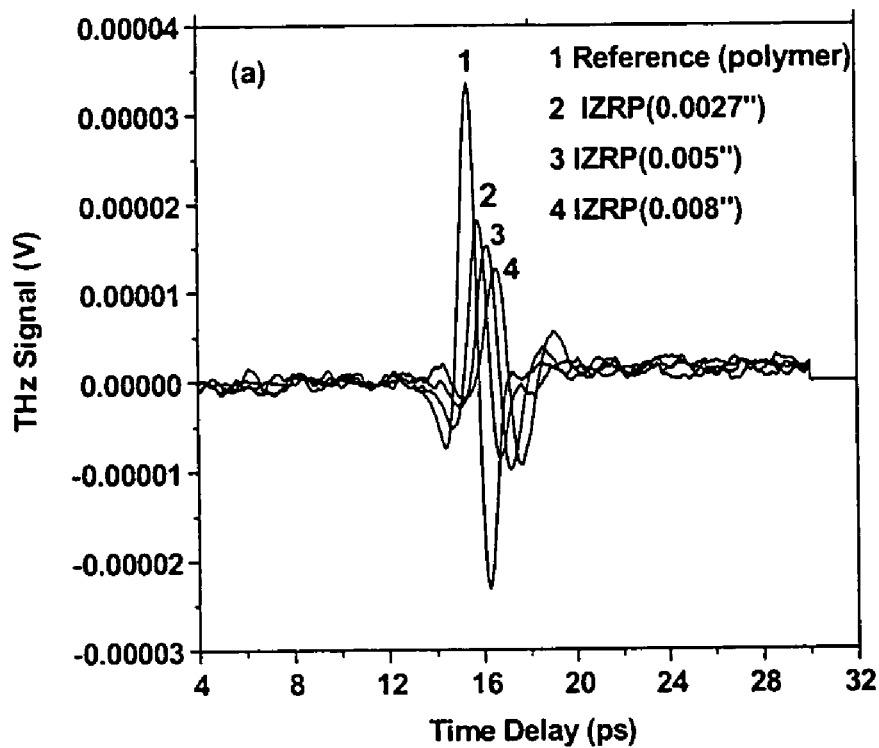
FIG. 7 is a graph illustrating THz temporal profiles of inorganic zinc rich primer (Dimetcote D9 HS) after passing through a pure polymer polyethylene substrate as reference.

FIG. 7 is a graph illustrating the THz temporal profiles of inorganic zinc rich primer (Dimetcote D9 HS) after passing through a pure polymer polyethylene substrate as reference. The thickness of the primers are 0.0027", 0.005" and 0.008", respectively.

Figure 8:
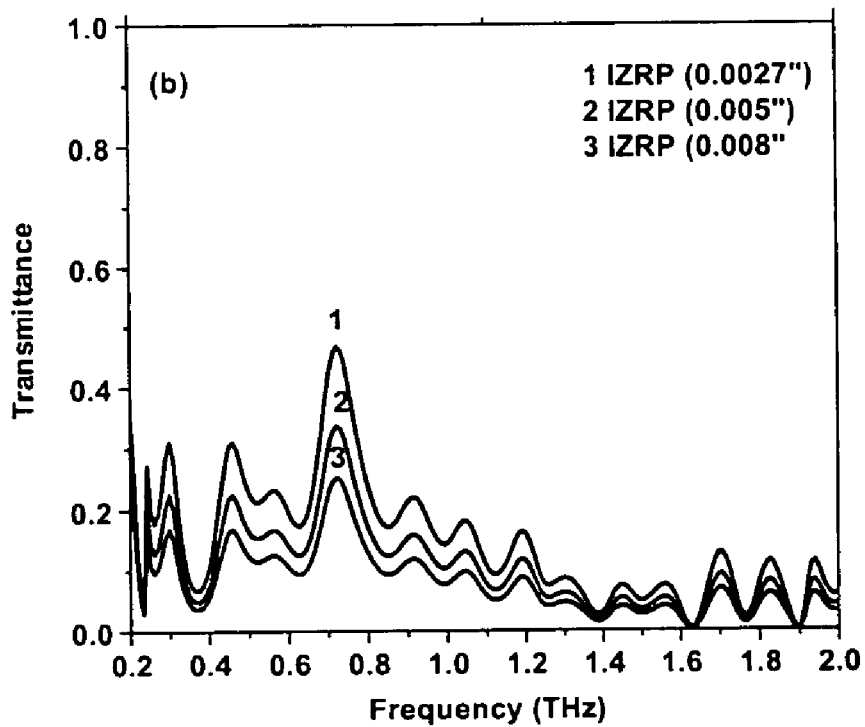
FIG. 8 is a graph illustrating THz transmitted profiles through primer films with different thickness in the frequency range 0.2 to 2.0 THz.

FIG. 8 is a graph illustrating the THz transmitted profiles through primer films with different thickness in the frequency range 0.2 to 2.0 THz. At 0.7 THz, the transmission is more than 20%.

Figure 9:
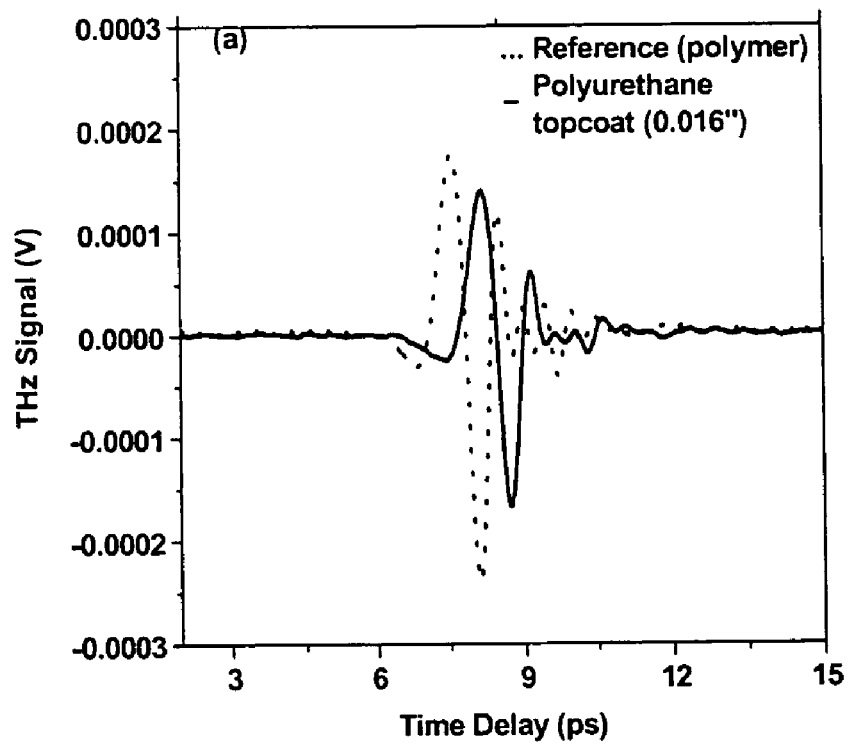
FIG. 9 is a graph illustrating THz temporal profiles for polymer polyurethane topcoat (Mil-PRF-85285, type I color 35237 blue) (0.016") (#31)

FIG. 9 is a graph illustrating the THz temporal profiles for polymer polyurethane topcoat (Mil-PRF-85285, type I color 35237 blue) (0.016") (#31).

Figure 10:
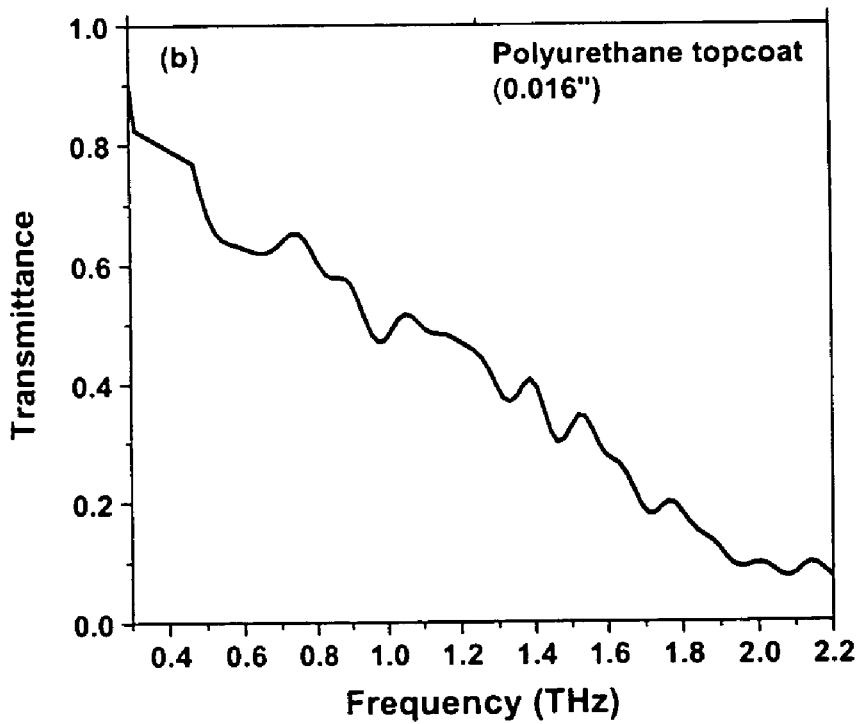
FIG. 10 is a graph illustrating a transmittance curve of a polyurethane topcoat (Mil-PRF-85285, type I color 35237 blue) in the frequency range 0.2–2.3 THz.

FIG. 10 is a graph illustrating the transmittance curve of polyurethane topcoat (Mil-PRF-85285, type I color 35237 blue) in the frequency range 0.2–2.3 THz. The transmission through the coating is from 20% to 80%.

As described above, the present application sets forth a THz-TDS scanning system that can be used to detect and image material abnormalities beneath zinc rich primer and metallic based paints, which NIR and MIR pulses could not penetrate. Accordingly, the THz transmission can pass through this type of paint to detect corrosion, defects, and/or cracks on a surface of structure.

While the invention has been shown and described with reference to certain preferred embodiments thereof, it will be understood by those skilled in the art that various changes in form and details may be made therein without departing from the spirit and scope of the invention as defined by the appended claims.

What is claimed is:

1. A method for non-destructively detecting material abnormalities beneath a coated surface, comprising the steps of:
   illuminating an area of a coated surface by a terahertz (THz) light source, the coating being metallic-based and fully penetrable only by radiation having a frequency range of from about 0.2 to about 2.0 THz;
   detecting light reflected from the illuminated area of the coated surface; and
   imaging the surface below the illuminated area of the coated surface.

2. The method as recited in claim 1, further comprising displaying a 2-D image on a display.

3. The method as recited in claim 1, further comprising imaging a next area of the coated surface.

4. The method as recited in claim 3, wherein the step of imaging the next area comprises moving the THz light source and a THz detection unit in at least one of X and Y directions.

5. The method as recited in claim 1, wherein the surface is metal.

6. The method as recited in claim 1, wherein the coating is one of a paint and a primer.

7. The method as recited in claim 6, wherein the coating includes zinc (Zn).

8. The method as recited in claim 6, wherein the material abnormalities include at least one of corrosion and cracks on the coated surface and are detected by processing unit.

9. The method as recited in claim 1, wherein the abnormalities include at least one of deterioration, corrosion, and cracking areas.

* * * * *